US012579829B2

(12) United States Patent
Brasch et al.

(10) Patent No.: US 12,579,829 B2
(45) Date of Patent: Mar. 17, 2026

(54) APPLICATION DEVELOPMENT ENVIRONMENT FOR BIOLOGICAL SAMPLE ASSESSMENT PROCESSING

(71) Applicant: BECTON, DICKINSON AND COMPANY, Franklin Lakes, NJ (US)

(72) Inventors: Michael A. Brasch, Southport, NC (US); Curtis M. Gosnell, Fallston, MD (US); Timothy M. Wiles, Ocean Isle Beach, NC (US); Raphael Rodolphe Marcelpoil, Corenc (FR); Bas Nieuwenhuis, Drenthe (NL); Trienko Marten Van Der Kaap, Drachten (NL); Michael Bois, Brooklyn, NY (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 212 days.

(21) Appl. No.: 18/214,874

(22) Filed: Jun. 27, 2023

(65) Prior Publication Data

US 2023/0360415 A1    Nov. 9, 2023

Related U.S. Application Data

(62) Division of application No. 16/753,667, filed as application No. PCT/US2018/054368 on Oct. 4, 2018, now Pat. No. 11,727,699.

(Continued)

(51) Int. Cl.
*G06K 9/00* (2022.01)
*C12M 1/34* (2006.01)
(Continued)

(52) U.S. Cl.
CPC ......... *G06V 20/698* (2022.01); *C12M 1/3446* (2013.01); *C12M 41/36* (2013.01);
(Continued)

(58) Field of Classification Search
None
See application file for complete search history.

(56) References Cited

U.S. PATENT DOCUMENTS

| | | |
|---|---|---|
| 5,694,478 A | 12/1997 | Braier et al. |
| 2008/0052112 A1 | 2/2008 | Zahlmann et al. |

(Continued)

FOREIGN PATENT DOCUMENTS

| | | |
|---|---|---|
| CN | 1321773 A | 11/2001 |
| CN | 102414716 A | 4/2012 |

(Continued)

OTHER PUBLICATIONS

First Office Action issued in corresponding CN application No. 2018800781337 on Apr. 26, 2024, p. 15.

(Continued)

*Primary Examiner* — SJ Park
(74) *Attorney, Agent, or Firm* — Botos Churchill IP Law LLP

(57) ABSTRACT

A system and method for developing applications (Apps) for automated assessment and analysis of processed biological samples. Such samples are obtained, combined with nutrient media and incubated. The incubated samples are imaged and the image information is classified according to predetermined criteria. The classified image information is then evaluated according to Apps derived from classified historical image information in a data base. The classified historical image information is compared with the classified image information to provide guidance on further processing of the biological sample through Apps tailored to process provide sample process guidance tailored to the classifications assigned to the image information.

25 Claims, 6 Drawing Sheets

Related U.S. Application Data

(60) Provisional application No. 62/568,579, filed on Oct. 5, 2017.

(51) Int. Cl.

| | | |
|---|---|---|
| *G06F 16/58* | (2019.01) | |
| *G06N 7/01* | (2023.01) | |
| *G06T 7/00* | (2017.01) | |
| *G06V 20/69* | (2022.01) | |

(52) U.S. Cl.
CPC .......... *G06F 16/5866* (2019.01); *G06N 7/01* (2023.01); *G06T 7/0016* (2013.01); *G06T 2207/10056* (2013.01); *G06T 2207/30024* (2013.01); *G06V 2201/03* (2022.01)

(56) References Cited

U.S. PATENT DOCUMENTS

| | | | |
|---|---|---|---|
| 2008/0310692 | A1 | 12/2008 | Robinson et al. |
| 2009/0105092 | A1 | 4/2009 | Lipkin et al. |
| 2010/0331641 | A1 | 12/2010 | Bangera et al. |
| 2012/0009558 | A1 | 1/2012 | Armstrong et al. |
| 2013/0109051 | A1 | 5/2013 | Li et al. |
| 2014/0314300 | A1 | 10/2014 | Kaufman et al. |
| 2015/0299639 | A1 | 10/2015 | Kleefstra et al. |
| 2015/0339513 | A1 | 11/2015 | Bolea |
| 2016/0033508 | A1 | 2/2016 | Dittamore |
| 2017/0013181 | A1 | 1/2017 | Marcelpoil et al. |
| 2017/0178321 | A1 | 6/2017 | Nieves Alicea et al. |
| 2017/0260564 | A1 | 9/2017 | Lagarrigue-Charbonnier et al. |
| 2018/0089828 | A1* | 3/2018 | Wiles ..................... C12M 41/46 |

FOREIGN PATENT DOCUMENTS

| | | | |
|---|---|---|---|
| CN | 103261435 | A | 8/2013 |
| CN | 103518224 | A | 1/2014 |
| CN | 103616383 | A | 3/2014 |
| CN | 104502317 | A | 4/2015 |
| CN | 105335982 | A | 2/2016 |
| CN | 105593359 | A | 5/2016 |
| CN | 105671122 | A | 6/2016 |
| CN | 106127264 | A | 11/2016 |
| CN | 106485313 | A | 3/2017 |
| EP | 2731051 | A1 | 5/2014 |
| JP | H09187270 | A | 7/1997 |
| JP | 2012075409 | A | 4/2012 |
| JP | 2014039520 | A | 3/2014 |
| JP | 2015536140 | A | 12/2015 |
| WO | 2015080001 | A1 | 6/2015 |
| WO | 2015114121 | A1 | 8/2015 |
| WO | 2016172527 | A2 | 10/2016 |
| WO | 2016172532 | A2 | 10/2016 |

OTHER PUBLICATIONS

Liu, Bing , "Analysis of Quality Control of Microbial Testing Medium", J. Medical Forum, No. 3, Full Text, Mar. 30, 2016 (Englsih abstract only).

Wang, Xuewen , et al., "Problems and Intervention Measures in Microbial Specimen Collection", Shanghai Nursing, No. 1, Full text, Jan. 20, 2009 (Englsih abstract only).

Zheng, Hui , et al., "Colonies Detection and Screening with Canny Based Algorithm", Shandong Science, No. 4, Full Text, Aug. 15, 2009 (Englsih abstract only).

Chinese Notification of Second Office Action issued in corresponding CN application No. 201880078133.7 on Nov. 7, 2024.

Supplemental Search Report issued in corresponding CN application No. 2018800781337 on Nov. 7, 2024., pp. 5.

JP Office Action issued in corresponding JP application No. 2023-136923 on Oct. 3, 2024., pp. 8.

Radke, SM , "A microfabricated biosensor for detecting foodborne bioterrorism agents", IEEE Sensors Journal, vol. 5,, No. 4, pp. 744-750 Aug. 1, 2005.

Canadian Office Action issued in Canadian Patent Application No. 3,077,590 on Apr. 14, 2025, pp. 5.

Canadian Office Action issued in CA application No. 3,077,590 on Dec. 20, 2023., pp. 5.

International Preliminary Report (IPRP)and Written Opinion issued in corresponding PCT application No. PCT/US2018/054368 on Apr. 7, 2020.

Communication issued in corresponding European Patent Application No. 18797217.9 dated Jul. 13, 2023 (7 pp.).

Office Action from corresponding Australian Application No. 2018346409 dated Jan. 6, 2023 (4 pp.).

International Search Report issued in corresponding PCT application No. PCT/US2018/054368 on Feb. 5, 2019, p. 14.

Croxatto, A. , et al., "Laboratory automation in clinical bacteriology: what system to choose?", Clinical Microbiology and Infection., vol. 22, No. 3, XP055545799,, (Mar. 1, 2016), pp. 217-235.

Mutters, Nico T., et al., "Performance of Kiestra Total Laboratory Automation Combined with MS in Clinical Microbiology", Annals of Laboratory Medicine, vol. 34, No. 2, XP055522844, (Jan. 1, 2014), pp. 111-117.

Notice of Allowance issued in Chinese Application No. 2018800781337 on Jul. 28, 2025., pp. 6.

Article 94(3) EPC issued in EP application No. 18797217.9 on Sep. 1, 2025, pp. 4.

Notice of Reasons for Refusal issued in JP application No. 2020-519433 on Jul. 22, 2025, pp. 5.

Examination Report No. 1 issued in AU application No. 2024200085 on Jul. 24, 2025, pp. 2.

* cited by examiner

TARGET ORGANISMS WITH PRESUMPTIVE IDENTIFICATIONS AND THE ASSOCIATED MEDIA

| Category | Organism | BLOOD AGAR TSA AND COLUMBIA | MacConky | CHOCOLATE | CHROMagar ORIENTATION | CHROMagar MRSA | CLED | CNA | HEXKTOEN | XLD | SS AGAR |
|---|---|---|---|---|---|---|---|---|---|---|---|
| MISCELLANEOUS | NEISSERIA | | | X | | | | | | | |
| MISCELLANEOUS | HAEMOPHILUS | | | X | | | | | | | |
| MISCELLANEOUS | YEAST | X | | | | | | | | | |
| GRAM POSITIVE COCCI | α STREP | X | | | | | | X | | | |
| GRAM POSITIVE COCCI | β STREP | X | | | X | | | X | | | |
| GRAM POSITIVE COCCI | ENTEROCOCCUS | X | | | X | | X | X | | | |
| GRAM POSITIVE COCCI | COAG NEG STAPH | X | | | | | | X | | | |
| GRAM POSITIVE COCCI | MRSA | | | | | X | | | | | |
| GRAM POSITIVE COCCI | S. AUREUS | X | | | | X | | | | | |
| GRAM NEGATIVE RODS | OTHER GNR | X | X | X | X | | X | | X | X | |
| GRAM NEGATIVE RODS | SERR\CITRO\KLEB\ENTERO | | X | | X | | | | | | |
| GRAM NEGATIVE RODS | SALMONELLA/SHIGELLA | | X | | | | | | X | X | X |
| GRAM NEGATIVE RODS | PROT/MORG PROV | X | X | | X | | | | | | |
| GRAM NEGATIVE RODS | PS. AER | | X | | | | | | | | |
| GRAM NEGATIVE RODS | E. COLI | X | | | X | | X | | | | |

FIG.3

TARGETED MEDIA WITH THE ASSOCIATED SPECIMEN TYPES

| | URINE | STERILE FLUIDS AND TISSUE | SUPERFICIAL WOUNDS | RESPIRATORY | THROAT | GASTRO-INTESTINAL | UROGENTIAL | SCREENING (NasoPharyngeal, RECTAL, etc...) |
|---|---|---|---|---|---|---|---|---|
| TSA BAP AND COLUMBIA BAP | X | X | X | X | X | X | X | |
| MacConkey | X | X | X | X | | X | X | |
| CHOCOLATE | | X | X | X | | | X | |
| CNA | X | | X | | | | | |
| CLED | X | | | | | | | |
| SABOURAUD DEXTROSE AGAR | X | | | X | | | X | |
| CHROMagar ORIENTATION | X | | | | | | | |
| HECKTOEN | | | | | | X | | |
| XLD | | | | | | X | | |
| SS AGAR | | | | | | X | | |

| | URINE | STERILE FLUIDS AND TISSUE | SUPERFICIAL WOUNDS | RESPIRATORY | THROAT | GASTRO-INTESTINAL | UROGENTIAL | SCREENING (NasoPharyngeal, RECTAL, etc...) |
|---|---|---|---|---|---|---|---|---|
| CHROMagar MRSA | | | X | | | | | X |
| CHROMagar ESBL | | | | | | | | X |
| CHROMagar CPE | | | | | | | | X |
| SELECTIVE STREP AGAR | | | | | X | | | |

CELLS INDICATE CRITICAL MEDIA TYPES

FIG.4

APPLICATION DEVELOPMENT ENVIRONMENT FOR BIOLOGICAL SAMPLE ASSESSMENT PROCESSING

CROSS-REFERENCE TO RELATED APPLICATION

This application is a divisional of U.S. patent application Ser. No. 16/753,667, filed Apr. 3, 2020, now allowed, which application is a national phase entry under 35 U.S.C. § 371 of International Application No. PCT/US2018/054368, filed Oct. 4, 2018, which claims the benefit of the filing date of U.S. Provisional Patent Application No. 62/568,579, filed Oct. 5, 2017, the disclosures of which are hereby incorporated by reference herein.

BACKGROUND OF THE TECHNOLOGY

There is increased focus on digital imagery of culture plates such as for detection of microbial growth, colony counting and/or identification. Systems and techniques for imaging plates for detecting microbes are described in PCT Publication No. WO2015/114121, WO 2016/172527, and WO 2016/172532, the entireties of which are incorporated by reference herein. Using such techniques (also referred to herein as Kiestra Systems), laboratory staff is no longer required to read plates by direct visual inspection. Shifting laboratory workflow and decision-making to analysis of digital images of culture plates can also improve efficiency.

Although significant progress has been made regarding imaging technologies, it is still sought to extend such imaging technologies to support an automated workflow and/or automated diagnostic processes. In this regard, it is desirable to develop techniques that may automate interpretation of culture plate images (e.g., identification of growth, identification of species, susceptibility testing, antibiotic sensitivity analysis etc.) and determine the next steps to be performed based on the automated interpretation. However, development of automated image processing logic (e.g., software) for diagnostic indications can be time consuming given the diversity of specimen types and organism taxa.

BRIEF SUMMARY OF THE TECHNOLOGY

Disclosed herein is a system for evaluating biological specimens for the presence of pathogens, the identity of those pathogens and other related analysis and evaluation. The objectives of the systems are speed of analysis, accuracy of the analysis and process automation. Such systems typically obtain digital images of specimens disposed on nutrient media and incubated to discern evidence of microbial growth, such growth providing an indication of the presence of pathogens in the biological specimen. Such systems are described herein as the Kiestra Systems and include apparatus such as a camera and lighting to obtain one or more images of the incubated specimen, bar code readers for the specimen containers (e.g. petri dishes that contain inoculated plated media), etc.

Such systems communicate with and are controlled by one or more customer-centric Imaging Application (Imaging-related Apps or Apps). Such Imaging Apps may be software that utilize data derived from a collection of historic specimen images to analyze new specimen images for automated identification and/or diagnosis of disease state. The Apps can provide a clinical tool for rapid specimen characterization and reporting of results. The Apps link clinical specimens (from a clinical site), to non-patient identifying facts about the specimens (e.g., non-patient identifying specimen origin information like demographics), process conditions (e.g. incubation time and temperature), process materials or environment (e.g. nutrient media) and/or non-patient identifying test results for the specimen (no-growth of pathogens, growth or otherwise positive identification of the pathogens, enumeration of the identified pathogens). The facts and conditions are referred to collectively as analytical information herein. Classifying such analytical information in this manner ensures that only the most relevant historical processing information is used to develop an app. Therefore, each developed app is created for a narrowly defined purpose and only deployed when the specimen classifiers correspond to the app classifiers. It is advantageous if the data is not linked to information that would identify the patient (i.e. patient deidentification). In one embodiment, the system automatically deidentifies the specimen information and information in response to certain conditions. Deidentification includes providing metadata that links to non-patient identifying classifying information (e.g. geographic region from which the specimen was obtained, type of specimen, etc.) that, in effect, permits the data to be used in systems and methods that cannot retain confidential patient information. The system may include Apps that provide time series processing of images, classified/trained and tested diagnostic/evaluation algorithms and/or expert systems. An App may include a module wherein a module may be understood to be one or more processes or algorithms for a particular purpose using, for example, image metadata (metadata serves as the classifications described herein) and rules. In some cases, multiple modules may be implemented as a package. In some embodiments, the data may be stored in a data base that can be used to develop an App, train an App, certify an App, test an App, etc.

The system may provide image analysis processes that may incorporate best practices, addresses relevant specimen types and automated picking.

To significantly expedite time to market for valuable Imaging Apps, a multi-fold or modular system may be employed. Such a multi-fold system may include modules such as:

a) Define Best-Practice solutions linked to specific media used to culture the target microorganisms and the taxa of the target microorganisms that balance utility and development timelines. For example, test results and images linked to specific media or taxa are combined and used to develop applications that will evaluate new specimens classified with the same media and taxa. The Apps will require enough information to develop a reliable application but not require so much information that development of the app is delayed.

b) Align an algorithm development cadence (i.e. pace or speed) that maximally reuses existing algorithms.

c) Establish clinical collaboration sites that continuously generate images and associated meta-data from a diversity of specimen types, organism taxa, and best-practices media. That is, specimen information is obtained to build a database of information that can be used to train, or further train, the developed applications. This database of fully classified historical specimen information is referred to as the data lake herein.

d) Generate a database of images with defined criteria that can be applied to algorithm training and validation/clinical submission. The database may include information/data representing images of clinical specimens with linked manual/standard analysis of truth (quantitation, identifications, result interpretation) and classifications (select patient demographics, imaging time and conditions, media types, etc.). A database infrastructure provides sequestered data that can be accessed individually as appropriate for algorithm development, formal verification and validation (V&V), or clinical submission. This data generation allows for on-demand prioritization and development of Apps for specific specimen or media types.

e) Adopt a strategy for non-selective media that buckets classification reflecting colony complexity (i.e., pure colonies, predominant colonies or complex colonies); and for identification and sister colonies, the data delimited, for example, by the type of media (e.g., chromogenic media (i.e. CHROMagars)) for defined taxa (or those defined taxa with specific properties on a specific media type (i.e., hemolysis on BAP) or other information about conditions and reagents used to obtain the images and test results.

f) Limiting certain Apps only to certain imaging systems/apparatus (e.g., when a 25 mp camera is used, certain system capabilities are provided, but other imaging apparatus will provide other system capabilities). Again, delimiting the Apps to use in certain narrowly prescribed contexts (e.g. sample type, media type, taxa type, camera type) and only using data to develop the Apps that corresponds to the prescribed context provides an App that is more likely useful and accurate for the specimens that the app is used to evaluate.

The Apps described herein can be further developed and refined as specimens, media and organisms are validated and obtain regulatory approval. For example, a quadrant quantitation App could be implemented initially for throat swabs and wound, and later for perianal or other specimen types as more specimens are processed. This ongoing training/development of the Apps provides a robust cadence of new Imaging Apps with increasing usefulness. For example, as more images are evaluated, the App "learns" how to differentiate colonies from background in the image of the plated culture. Processing image information to differentiate pixels associated with the image of the colony from the pixels associated with the image of the background are described in the Kiestra Systems referenced previously herein.

Also described herein is a development system that provides high-value software solutions while reducing time to market and maximizing utilization of resources. An important component of the system may involve initiating a collaboration program that engages select clinical sites running imaging systems (e.g., Kiestra Systems) to gather clinical specimen imaging information that is classified by association with meta-data for development (algorithm training) and validation (submission-ready) purposes. This collection of data may feed automated algorithm refinement, improving performance and decreasing development time. Validation uses a sequestered collection of images in the database. These data can also be reused as additional features are implemented. However, the information is only deployed when the data classification corresponds to the App classification/purpose. This approach creates substantial efficiency, flexibility in App scope (i.e., versioning) and a highly-valuable resource.

For non-selective media, classification buckets are created that characterize the complexity of the population to identify cultures as no growth, pure, predominate or complex/mixed rather than attempting to identify all sister colonies of all taxa on all media types. Sister colony identification is technically very challenging and time consuming, particularly on non-CHROMagar media. Mixed cultures typically require expert knowledge to interpret, and even with a level of automated image analysis, would likely require review for confirmation and release. By using the pure, predominate and complex/mixed categories most specimens can be characterized and those with pure or predominate colony populations can be automatically worked up with a high degree of confidence. These colonies can then be chosen by the App for automated picking by a picking system. This approach largely renders the need to individually characterize and define specifications of each specimen type (e.g., sputum, wound, swab, etc.) by/verses a particular pathogen, to a more generic classification strategy that efficiently leverages the imaging algorithms and enables most specimen types to be characterized.

Example Imaging Apps are summarized below. Such applications may include
MRSA screening Imaging App;
Urine 2.0 Imaging App;
Rapid detection Imaging App; and
Quadrant quantitation Imaging App.

For example, in response to a MRSA (Methicillin-resistant *Staphylococcus Aureus*) screening analysis, the following actions may include: (i.e. for a negative MRSA screening result): i) empiric treatment with a certain set of antibiotics not used with resistant *Staph aureus*; ii) not sequestering or specifically managing the patient; iii) proceeding with a certain next medical step such as surgery; iv) the ordering of certain additional diagnostic tests; and v) guidance in selection of a certain set of likely effective antibiotics for determination of antibiotic susceptibility testing. An application developed according the method described herein can guide a user to some or all of the above actions based on historical analysis of prior specimens that share certain predetermined criteria with the specimen being evaluated by the App.

Actions from a Rapid Detection Imaging App may include: i) communicating to the treating physician the detection of threshold levels of growth indicating infection many hours sooner than standard methods of practice; ii) initiating diagnostics that rapidly determine the identification of growing pathogens (e.g., via MALDI-tof); iii) communicating the pathogen identification to the physician substantially earlier than standard practice; iv) initiating diagnostics for determination of antimicrobial susceptibility and communicating antibiotic susceptibility profiles substantially sooner than current practices. These objectives are accomplished by using prior images and the results of that image analysis to inform analysis of the present image. The prior images must be classified to develop an App that is sufficiently skilled and reliable to be used to evaluate the present image. Note that, if the image analysis performed by the App results in a positive detection of microbial growth, in one embodiment the App can communicate with an analyzer that will receive the specimen under evaluation and identify the colony or colonies on the specimen to be picked for further analysis. The App can either instruct downstream process or control downstream processing Such downstream processing includes: i) preparing a suspension of the one or more picked colony into a pre-determined buffer or solution; ii) adjustment of said suspended cell suspension to a predetermined cell concentration; iii) the spotting of said cell suspension to a substrate (e.g., MALDI Plate); iv) overlaying of said spots with one or more reagents including, for example, MALDI matrix solution, extraction chemicals; v) distributing one or more aliquots of said cell suspension into wells of an antimicrobial susceptibility plate for determination of susceptibility profiles to a series of antibiotics at various concentration; and vi) distribution into suspensions for analysis by PCR, sequencing or other molecular diagnostic tests. In alternative embodiments the App instructs but does not control follow-on sample processing/analysis.

In order for the Apps developed according to the methods described herein to be deployed to control processes and evaluate specimens, the Apps must be developed using relevant data and analysis. Methods and equipment that can be used to obtain relevant data and analysis include, clinical sites collecting images and reference data, that are used to build data sets for future Imaging Apps training and validations. See FIG. 1. This typically involves resources to identify, initiate, and manage the collaborations and data. Software tools gather data and meta-data from the clinical sites. Technical resources may need to be provided in the lab to generate and assign the classifications as metadata, such as from Image Processing, not normally acquired in typical clinical workup.

The digital cameras (which are conventional cameras with good megapixel resolution, e.g., 5 MP, 25 MP, etc.) may be implemented for adequate performance for early growth/no growth and presumptive identifications (IDs). For example, for a Colony greater than or equal to 5 mm diameter detected by the imaging module or apparatus that captures the digital image of the inoculated plate, this data could be combined with the Growth/No Growth Detection to indicate when growth occurs with sufficient colony size for further processing. The imaging apparatus may itself be an App that performs analysis of the digital image, such as described in the Kiestra Systems references elsewhere herein. According to those systems and methods, colonies are differentiated from background and from that image analysis the density of the colonies on the inoculate plate is determined and communicated to an App that will determine further actions in response to the image analysis. This information could then be used by the App to determine what colony to pick from the image automatically (without an operator reading the plate or identifying the colony for pick). The Apps are developed and deployed for specific plate environments. For example, pure plates (one colony type) and predominant plates (more than one colony type but predominantly one colony type) can have representatives of each colony type indicated by the purity plate module with associated rules that determine further workup. Plates determined to be complex are processed by a different App (or an App that fires different rules). A pre-determined number of each colony type could be designated for automatic identification (ID) and Antibiotic Susceptibility Testing (AST) workup on an ID/AST module that may involve an automatic picking system/robot.

To decrease product development cost and reduce time to market Best Practices support may be adopted. Specific media (below) may be used to obtain optimal recovery and performance on the platform (e.g., BD Kiestra systems).

The system may involve processing of plated media readings performed in a lab. Plated media are prepared as described elsewhere herein. The media type and sample taxa are examples of specimen classifiers that inform the metadata linked to the specimen information. The selected App may provide presumptive ID with picking recommendations of only the pure or predominant colony types on the plate. Specimens with multiple clinically significant isolates are infrequent and often complex. Specimens identified as complex may be put into a mixed category for manual review and actioning.

A set of algorithms may be designed that are more generic rather than specific to an App configured for use with a specific type of specimen or the suspected target species contained in the specimen. These algorithm tools are not described in detail herein but can be developed and deployed by those skilled in the art. The algorithms are validated as a process for deployment in Apps designed to evaluate and process a range of specimen types. When such tools are not limited to specific specimen types, they can be used to review a larger number of plates or as building blocks of other Apps.

The system develops a set of tools that provide an overall capability that can be supplemented in the future as more specimen processing data (e.g. imaging data) is obtained and added to the database with the associated classifications. These tools will evaluate plates and provide a specific result independent of specimen type. A compilation of these results along with specimen and patient demographics will be processed by the App to provide an indication of the specimen quantity. This simplifies execution and leads to a faster time to market while providing the user with a level of flexibility. Development of a more generic toolbox of image analysis algorithms (together with the classification metadata, and rules termed a Module) that enable the App can be rapidly matured or optimized (for a particular specimen, for example) by deploying artificial intelligence algorithms such as neural networks, artificial neural networks or deep learning algorithms that use the classified specimen data in the database to make determinations about the subject specimen. As part of the exponential strategy, artificial intelligence may be employed that "automatically" determines what attributes of the image, and with what algorithms, to best provide the desired Module capability. Individual Modules may have sufficient value to be launched as an App, or multiple Modules may be packaged into an App. In some versions, a set of modules may be differentiated to make the following specimen analysis based on the specimen information obtained and its classification: (a) Growth/No Growth; (b) Semi-quantification; (c) Presumptive ID (d) Pure, Predominant, Complex (e) Antibiotic sensitivity (Kirby-Bauer test) (f) Sister colony locator.

Example applications (Apps) may include Key ID, Rapid Detection, CHROMagar ID 2.0, Quadrant Quantitation and Presumptive ID. These may be summarized as follows:

Key ID is a tool that identifies specific species on specific plates where any numbers of colonies are present. Any number of colonies typical of the Key ID app will be designated in pure or mixed cultures. Examples are:

1. MRSA screening on MRSA II;
2. Group A Beta Strep on BAP (Blood Agar Plate); and
3. Strep pneumoniae on BAP.

The Rapid Detection App provides rapid detection processing. Growth at any reading point can be used as a flag for growth detected as early as possible on any plate. The user selects the reading point that will serve as a flag, recognizing the trade-off between an earlier reading point that may be less reliable but delivers results more quickly and a later reading point which may be more reliable but take more time to detection. The action taken will be dependent on the reading points chosen and the rules invoked. Early detection may happen as early as 4 hours, but incubation periods of 6 hours, 8 hours or longer are contemplated. Incubation times for a particular specimen are readily ascertained by one skilled in the art. The system and method described herein is not limited to any particular incubation time. The Rapid Detection App is beneficial for rapid positives of critical specimens.

For example, growth is detected at 8 hours on a BAP plate. A rule would take these results and if the specimen type is CSF (Cerebrospinal fluid) the lab would be alerted immediately if the App determined that the specimen had growth on the plates because CSF is typically sterile. This determination requires the App to make some sort of alert in response to a determination that the CSF specimen is positive for pathogens. For other specimen types, i.e., sputum, early detection would have little value since almost all culture have normal flora. In these cases, no rule would be written for specimens so classified and no action would be taken by the App based on rapid detection. Thus, the type of plate and type of detection can trigger different automated processes.

Another embodiment is a CHROMagar ID App that quantitates urines or other specimen types. This App obtains classified image information that will enable the App to presumptively identify the pure or predominate colony type on CHROMagar Orientation. Mixed plates will also be identified but the App may fire different rules in response to the determination of a complex plate. Using the rules engine, the processed images of specimens can be sorted into several categories. Certain categories permit auto reporting of results. Those categories are described elsewhere in detail herein.

The Quadrant Quantitation and Presumptive ID app is a tool that will evaluate all positives to classify each as one of (1) no growth, (2) pure, (3) predominate or (4) complex and the overall quantity on the plate. The pure or predominate isolates will be presumptively identified and colonies identified for picking. In this case all cultures would be analyzed and would fall into several categories with some being auto reported and others sent for review. The plates with significant pathogens could be sent to other systems (e.g., picking or testing) for picking with no customer/clinician intervention. The Table in FIG. 3 is a listing of the target organism that will be presumptively identified on the referenced plates. The Table in FIG. 4 is a listing of plates commonly inoculated for specific specimens (Best Practices).

The environment (e.g., FIG. 1) may provide a Software Development Workflow. This development effort will focus on completing the workflow and implementing the detection of the organism groups in FIG. 3 on the target media in FIG. 4. The flowchart in FIG. 2 (FIG. 2A and FIG. 2B) outlines the general strategy for algorithm and software development for one or more Apps in support of an analytical workflow for digital image evaluation. All images of the inoculated and incubated culture plates are evaluated by the modules as outlined in FIG. 2A and FIG. 2B of FIG. 2 and described below. Each module evaluates a specific result or discrete group of results and is largely independent of specimen type. However, metadata associated with the specimen (which is used to classify the specimen) can also guide further processing (e.g., incubation instructions, imaging instructions, etc.). Such metadata can be read from a barcode on the specimen container (i.e. the plate or Petri dish). When results are available, processing by an expert system evaluates these results and recommends or takes the appropriate action. For example, when the App indicates that a specimen should be evaluated by AST, the expert system will provide guidance rules for the AST panel That guidance typically takes into consideration regulatory or guidance positions (i.e. by FDA or CLSI) as well as limitations on the proven abilities of the AST test platforms (i.e. limitations). An expert system is provided with a base set of rules. The App itself may also fire rules based on information that the App learns about the subject image of the subject specimen, even though the App is not, in and of itself, an expert system. These rules could be edited or additional rules developed by the user specific to their institution.

Once the plates are evaluated and results are combined at the specimen level another set of rules would drive auto reporting, user, Laboratory Information System (LIS) or Laboratory Information Management System (LIMS) alerts, and send significant isolates to a worklist or to a picking system such as for ID/AST testing.

By targeting organisms on media independent of the specimen type complete systems may be developed more efficiently and rapidly. For example, *E. coli* may be considered the same genus and species no matter the specimen source for the *E. coli*. Regulatory approval of some Apps by specimen type could be difficult since positives for some specimens (i.e. CSF and other sterile sites) are rare and therefor there would not be sufficient historical sample processing/image data from which to develop an App that would be clinically reliable. However, over a period of time and with the benefit of images and test results from those images obtained from a variety of sources (i.e. clinical trials, regulatory submissions), Apps for even rare specimens can be developed.

One embodiment is a method for processing a biological sample including the steps of obtaining a biological sample, combining the biological sample with nutrient media, incubating the biological sample, obtaining a digital image of the incubated biological sample, classifying the digital image according to analytical criteria selected from the group including of specimen origin information, clinical sample criteria, process materials and process conditions, obtaining data from historical digital images of incubated biological samples on nutrient media that share at least one of the analytical criteria assigned to the digital image and using the historical digital image data to output an instruction to a user for further processing of the biological sample.

The specimen origin information includes geographic information regarding the biological sample source and the type of biological sample. The process materials include the type of nutrient media. The historical digital image data is classified by at least one of specimen type, organism taxa or culture media type. The method further includes analyzing the digital image data and determining, from the analyzed data if the digital image reflects microbial growth. In response to a determination that the digital image does not show microbial growth, the method outputs an indication of no microbial growth. In response to determining that there is an indication of microbial growth, the method performs the step of determining if the specimen is a sterile specimen and identifying one or more coordinates of a colony of microorganisms in the image that was a basis for the indication of microbial growth. In response to determining that the specimen is sterile, the method includes the further step of indicating that the specimen is a high value positive and sending instructions to further process the specimen. Examples of further processing includes identification (ID) testing, antibiotic susceptibility testing or both. The coordinates of an object in the image classified as a colony are communicated to a module that forwards those coordinates to a picking apparatus that will pick the colony from the biological sample. A module may be an App or a combination of Apps as described herein. The biological sample is transferred to the picking apparatus and the colony is picked from the biological sample wherein the steps of transferring and picking are either controlled by the module or the module has issued an instruction to perform such steps. In response to determining that the specimen is not sterile, the historical image data is compared with the image data to identify a specific predetermined species of microorganism in the digital image of the incubated biological sample. The step of comparing is performed by the module, and, if the module determines that the specific predetermined species of microorganism is present in the image data, the module reports the identification of the specific predetermined species. When such a determination is made the module flags the specimen for further review.

The module compares the historical image data with the digital image of the incubated biological sample and determines an amount of microbial growth where the comparing and determining steps are performed in the module in communication with the imaging apparatus that obtained the digital image of the incubated biological sample. According to the method, a module or App determines if the microbial growth is one of pure colonies, predominant colonies, or complex colonies by communicating the digital image of the incubated biological sample to a module that determines a growth level as a vector of three probabilities. In response to a determination that the colony is pure, the module reports that the plate is pure. If the growth on the pure plate exceeds a predetermined threshold growth the biological sample is identified as a high value positive and the module communicates that information to a user of the system. The module, having received the coordinates of the colony from the imaging apparatus, will communicate the coordinates to a picking apparatus that will pick the colony from the biological sample. The method may also include transferring the biological sample to the picking apparatus and picking the colony from the biological sample where the steps of transferring and picking are controlled by the module or requested or required by the module. If the module determines that the growth does not exceed the predetermined threshold the module provides a presumptive identification of the colony based on comparing an image of the colony provided to the module with the historical image data accessed by them module. In response to the determination the module performs the further step of reporting the presumptive ID to a user.

If the module determines that the growth does not exceed the predetermined threshold the module performs the further step of reporting to a user that the complex sample does not meet or exceed the positive growth threshold. In response to a determination that the colony is predominant, the module provides a presumptive identification of the colony based on comparing an image of the colony provided to the module with the historical image data accessed by the module. The module performs the further step of reporting the presumptive ID to a user.

If the module determines that the growth exceeds a predetermined threshold growth, the module identifies the sample as a high value positive. The method also includes alerting a user of the high value positive. The method may also include identifying the coordinates of the high value positive. The method may also include communicating the coordinates of a colony to a module that communicates the coordinates to a picking apparatus that will pick the colony from the biological sample. The method may also include the module controlling or issuing instructions to transfer the biological sample to the picking apparatus and picking the colony from the biological sample where the steps of transferring and picking are controlled by the module. The method may also include alerting a user that further review is required. If the module determines that the growth does not exceed the predetermined threshold the module performs the further step of reporting the presumptive ID to a user. In response to a determination that the colony is complex, the method further includes: reporting, from the module, that the plate is complex. The method may also include determining, by the module, if the growth exceeds a predetermined threshold growth. If the module determines that the growth exceeds the predetermined threshold growth, the method further includes: alerting a user that further review is required.

BRIEF DESCRIPTION OF THE DRAWINGS

FIG. 2 is an example flow diagram of an implementation with example Apps and their processes in a development environment according to an aspect of the disclosure.

FIG. 3 is a table illustrating an example of target organisms with presumptive identifications and the associated media.

FIG. 4 is table illustrating example targeted media with the associated specimen types.

DETAILED DESCRIPTION

Figure 1:
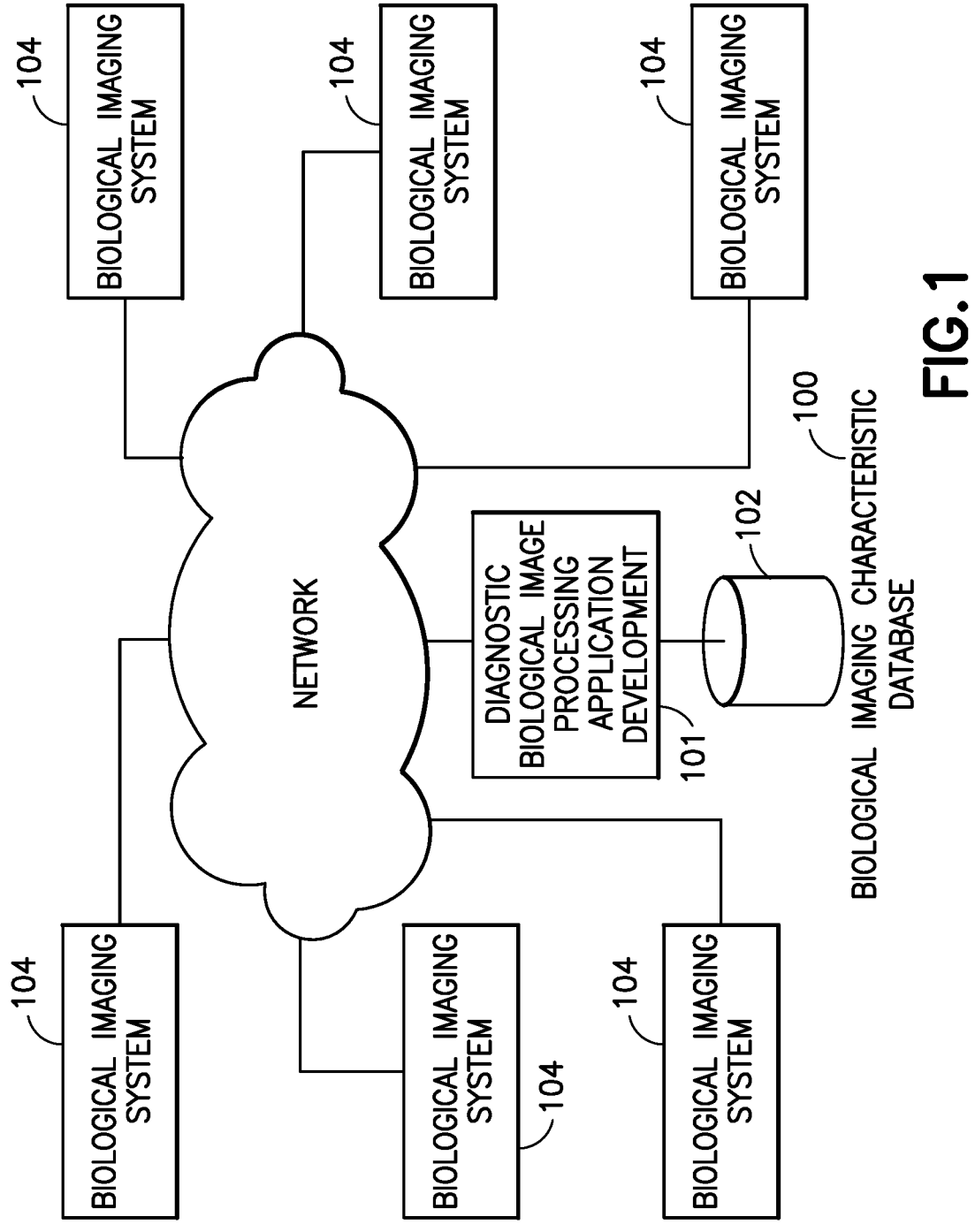
FIG. 1 is a block diagram illustrating an example system environment for biological image processing application development.

The present disclosure provides apparatus and methods of an environment for developing imaging applications for identifying and analyzing biological specimens such as microbial growth. Many of the methods described herein can be fully or partially automated, such as being integrated as part of a fully or partially automated laboratory workflow.

This document provides a description of the design and implementation of a system that accelerates delivery of automated imaging capabilities to biological imaging systems such as the BD Kiestra™ System. The imaging capabilities of such systems are enabled by a suite of hardware, software, analytical algorithms, and clinical rules. An example of one such commercialized system includes one or more digital cameras (e.g., 4 MP) with multiple illumination configurations that generate an optimized and standardized image based on an appropriate platform. The systems described herein are capable of being implemented in other optical systems for imaging microbiology samples. There are many such commercially available systems, which are not described in detail herein. One example may be the BD Kiestra™ ReadA Compact intelligent incubation and imaging system. The Kiestra™ ReadA compact is an automated incubator with an integrated camera and plate transport system that enables automated imaging of plates. The ReadA compact is commercially available. The ReadA compact also has integrated plate import and plate export devices that couple the incubator to other instruments for manipulation. Therefore, in some embodiments, in response to the analysis of the digital images by one or more of the Apps, the Apps can issue instructions and control the incubation of the relevant specimen under evaluation by the App. Other example systems include those described in PCT Publication No. WO2015/114121 and U.S. Patent Publication 2015/0299639, the entirety of which is incorporated by reference herein. Such optical imaging platforms are well known to those skilled in the art and not described in detail herein.

A series of Apps for the system can provide analysis of the images from most specimens, generated at various predetermined times, such as in the ReadA Compact. The system can enable downstream actioning of these plates-including automated release of no-growth and/or negative plates, and automated characterization of colonies for definitive ID and AST analysis.

At a high level, the imaging analysis tools (Imaging Apps) can be deployed to enable a collection of different results that provide substantial value to the lab and/or actionable clinical results. These Apps utilize one or more image analysis algorithms (Modules), as well as a set of rules that provide information on how to apply the Modules on specific media types and/or specific specimens. Certain Apps can also have associated Expert Systems, which overlay an additional set of rules on more basic App determinations, typically regulatory/clinical guidance, that inform recommendations for actioning and interpreting the result.

Developing Imaging Apps can utilize an iterative approach. A data lake is developed using either specimen information acquisition or images of clinical specimens being processed as normal practice in the clinical lab, or both. Algorithms are developed to model conclusions/instructions/outputs such as those illustrated in FIG. 2 (FIG. 2A and FIG. 2B) that can be drawn from the truths and classification information associated with a specimen image evaluated by the App. Validation and verification (V&V) of the App is performed by using a collection of predefined images with certain metadata requirements from the data lake that are marked for V&V analysis. The Apps are then subjected to a clinical study (which includes processing specimens to obtain images of those samples and evaluating the images of the specimens using the App) to both verify the App and train the App. The clinical studies do not require that a specific clinical site is used for the clinical study However, a biological image processing application development system 100, such as one illustrated in FIG. 1, may be implemented to leverage an exponential strategy with several components. The system 100 includes one or more of:

a) a set of toolbox applications, such as for processing system 101 with one or more processors, having generic algorithms and Modules that enable the App and can be rapidly matured or optimized (for a type of specimen, for example) by applying Artificial Intelligence algorithms such as neural networks, artificial neural networks, and other deep learning algorithms. Artificial intelligence may be implemented to "automatically" determine what attributes of an image, and with what algorithms, to best provide the desired Module capability.

b) critical to the development and deployment of the Apps described herein is a developed database 102, denominated a Data Lake herein, that comprises images of clinical specimens with linked manual/standard analysis of "truth" (i.e. facts regarding the mage such as colony quantitation, IDs, result interpretation, etc.) and image conditions, and in some cases patient demographic data (suitably disidentified). The images carry classification information in the form of metadata so that only relevant image data is used to develop a particular App. The Data Lake may be populated by clinical lab collaboration such as with imaging systems 104 that may optionally supply data to the database via a network.

Where the Data Lake is stored is largely a matter of design choice. The Data Lake can be stored locally or in a cloud. The data in the Data Lake can be partitioned. For example, the data in the Data Lake could be segmented depending on how the data is accessed and/or used. In one embodiment, one segment of the data in the Data Lake could be for algorithm training, another segment could be used for data verification or validation and yet another could be used for clinical submission.

The database of the system can store and provide classified data of these clinical images and also linked data, that can be pulled individually as appropriate for algorithm development, formal verification and validation, or clinical submission on demand. The App can be established with a level of global standardization including lab protocols, media types, imaging time, quantitation scoring, etc. Resources can supplement the generation of images and reference data (specimens and/or spiked/contrived samples) for specimens/organisms/conditions that are infrequently encountered in the clinical setting. This proactive strategy for data generation allows an almost on-demand prioritization and development of particular Apps for specific specimen or media types. The system architecture permits integration of the new modules into existing laboratory site software to ease release of new imaging diagnostic functionalities (Apps/modules/packages). This may be achieved by standardizing the interface between new Apps/modules/packages with existing/previous imaging software systems. In this regard, the Apps/modules/packages may be add-ons to system software such as a system software for an automated imaging system (e.g., in a processing system that controls any one or more of a plate/sample conveyor, incubator, camera, picking machine and/or related robotics, for moving such samples/plates within such automated laboratory cell/equipment etc.). Certain specimens determined to be negative for pathogens can be spiked with known pathogens and the subsequent image of the incubated, spiked specimen characterized as described herein. The images of the spiked specimens can then be used as a training set for Apps that can be used to evaluate and process less frequently occurring pathogens.

This approach can provide maximal flexibility in prioritization and the cadence of App development. It would also make it possible to provide early App performance metrics to help better understand the added value of an App, the synergies at the solution level, and enable earlier recognition. The Data Lake may be generated such as with one or more hospital systems that meet a list of Corporate Clinical Development (CCD) criteria (i.e. technical and medical information). Implementation provides the ability to store and classify the data, query, and audit the database; lab protocols that define the program and processes; training, monitoring, compliance, quality metrics etc. as is typical for a clinical trial-and may be done as part of the development of the Data Lake, rather than at the end of a typical product development process. The approach may implement dedicated clinical lab resources to determine certain plate results outside standard protocols, and to link images with analysis results to the Data Lake. Certain specimens, plate types or image acquisition time points may need to be run specifically to develop the Data Lake in special processes that may be independent of normal/typical lab practice. Thus, in some versions, the Data Lake database may comprise images of clinical specimens with linked manual/standard analysis of truth (e.g., quantitation, IDs, result interpretation) and metadata associated with classifications for the image (e.g., select patient demographics, imaging time and conditions, media types, etc.).

Figure 5:
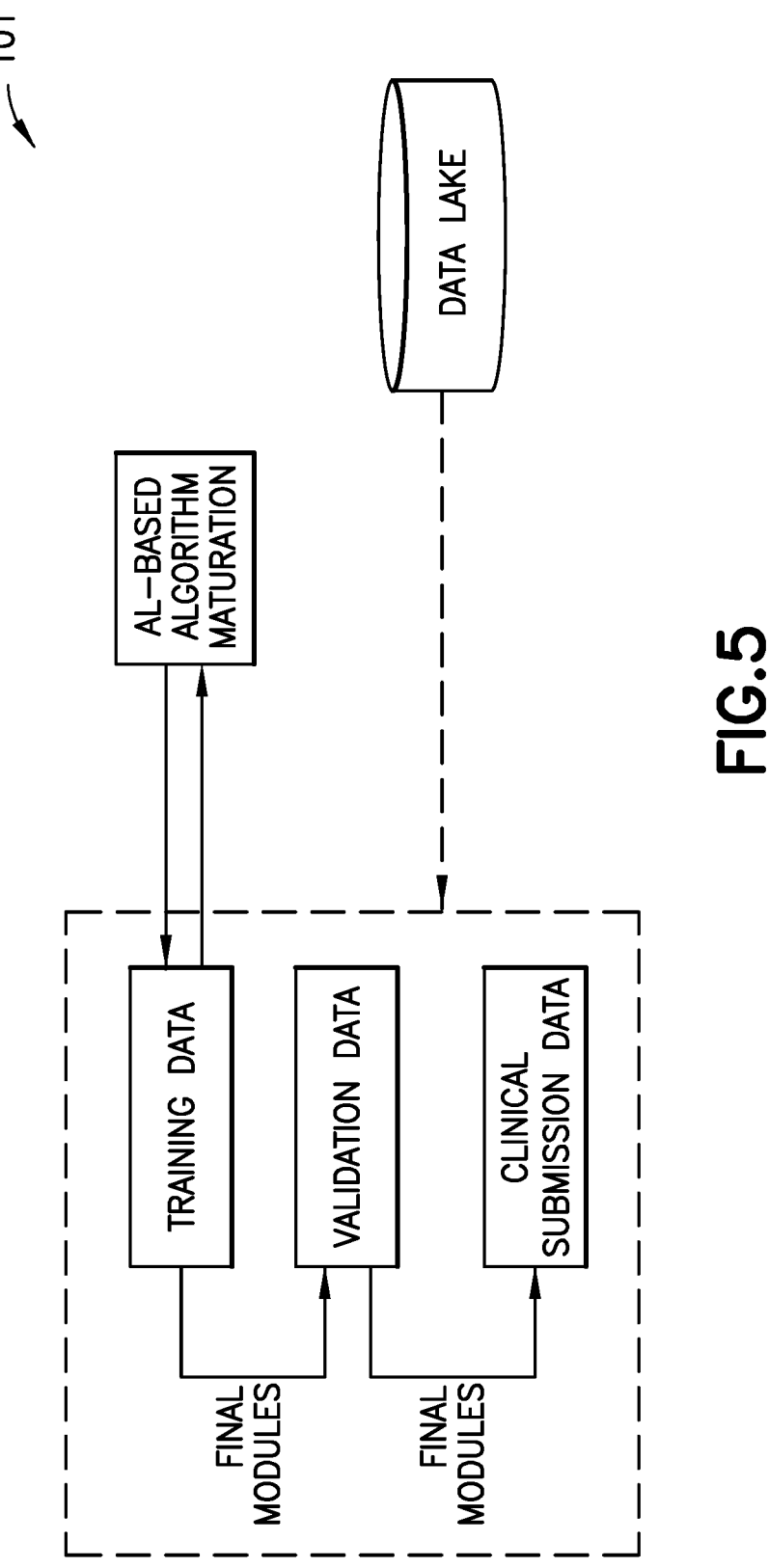
FIG. 5 is a schematic of processes that may be implemented in some versions of the present technology, such as in a processing system 101 of in FIG. 1, where the processing system may access data and/or algorithms of a Data Lake as discussed herein to develop Apps with a training process, validation process and/or clinical submission process. These processes may in turn employ information (e.g., updated data and algorithms) also derived from the Data Lake.

Establishment of both the algorithms and Data Lake may include a certain level of standardization. This will also define what any given App is validated for, and the analysis/instruction/output that may ultimately be obtained. Given the diversity of media types, vendors of media, and incubation times in use across labs globally, a "Best Practices" approach may be used to initiate this effort. Additional conditions may be added in the future by stocking the Data Lake with appropriate data. An example of a Media x Specimen matrix is summarized in FIG. 3. The table in FIG. 3 includes 12 media types. Note that Blood Agar, tryptic soy broth (TSA) and Columbia are grouped together as one media type. XLD is Xylose Lysine Deoxycholate Agar, SS agar is *Salmonella, Shigella* agar, CNA is Columbia Naladixic Acid Agar (CNA) and CLED is Cystine-Lactose-Electrolyte-Deficient agar. The listed media are well known to those skilled in the art as are the microorganisms known to be identifiable on the listed media. Thus, the standardization may include lab protocols, media types, imaging time, streak patterns, quantitation scoring, etc. that are classifications applied to the data for the database development and image analysis with reference to the data base/Data Lake/historical image information. This focuses validation efforts and minimizes time for development and allows lab to lab metrics, data sharing, etc. The use of the Data Lake as training data, validation data, clinical submission data, etc. for developing Apps is illustrated in FIG. 5.

To ensure database accuracy, population of the data into the database may involve independent human image analysis of images performed by several individuals, or plate analysis done manually by human technologists. Human readings may be compared with clinical laboratory reports. In some cases, a further image review may be involved for discrepant readings. Database input may involve de-identification of patient information from image related data. Review of images for data entry may involve human scoring of the growth on plates for pure, predominant, complex and no growth; quadrant quantitation.

Example Software Modules for Toolbox

In a typical example, the Data Lake may contain media plate images, linked to lab-determined quantitation (e.g., no growth, +, ++, +++). It may also contain identification (ID) of organisms determined to be of significance for the kind or type of specimen (such as ones that may be significant a trained clinical microbiologist). The Data Lake may also contain image-based metadata, and in some cases, patient demographic information. Organisms not routinely identified as pathogens (i.e., normal flora) may also be requested to be identified to facilitate algorithm development. Once populated, a portion of images will be leveraged to train and test appropriate algorithms toward App development.

At a high level, the imaging analysis tools can be deployed to enable a collection of different results that provide substantial value to the lab and/or actionable clinical results. These Modules (Mods) are comprised of one or more image analysis algorithms, as well as a set of rules that provide information on how to apply the Modules on specific media types and specific specimens. Some Modules, such as Screening-MRSA, may be implemented as an App. Other modules may more often be packaged with other Modules to provide a synergistic capability (for example, quadrant quantitation and purity will often be packaged as an App.) Some Apps can also have associated Expert Systems, which overlay an additional set of rules, typically regulatory/clinical guidance, that inform recommendations for actioning and interpreting the result (e.g. KB Zone described herein). Based on technical and clinical considerations, one or more Apps may also be bundled as components of a Launch Package depending on different clinical lab needs. It is also anticipated that some Apps will have versions (e.g., UCA V1.8 with FDA approval will become UCA 2.0).

Figure 2A:
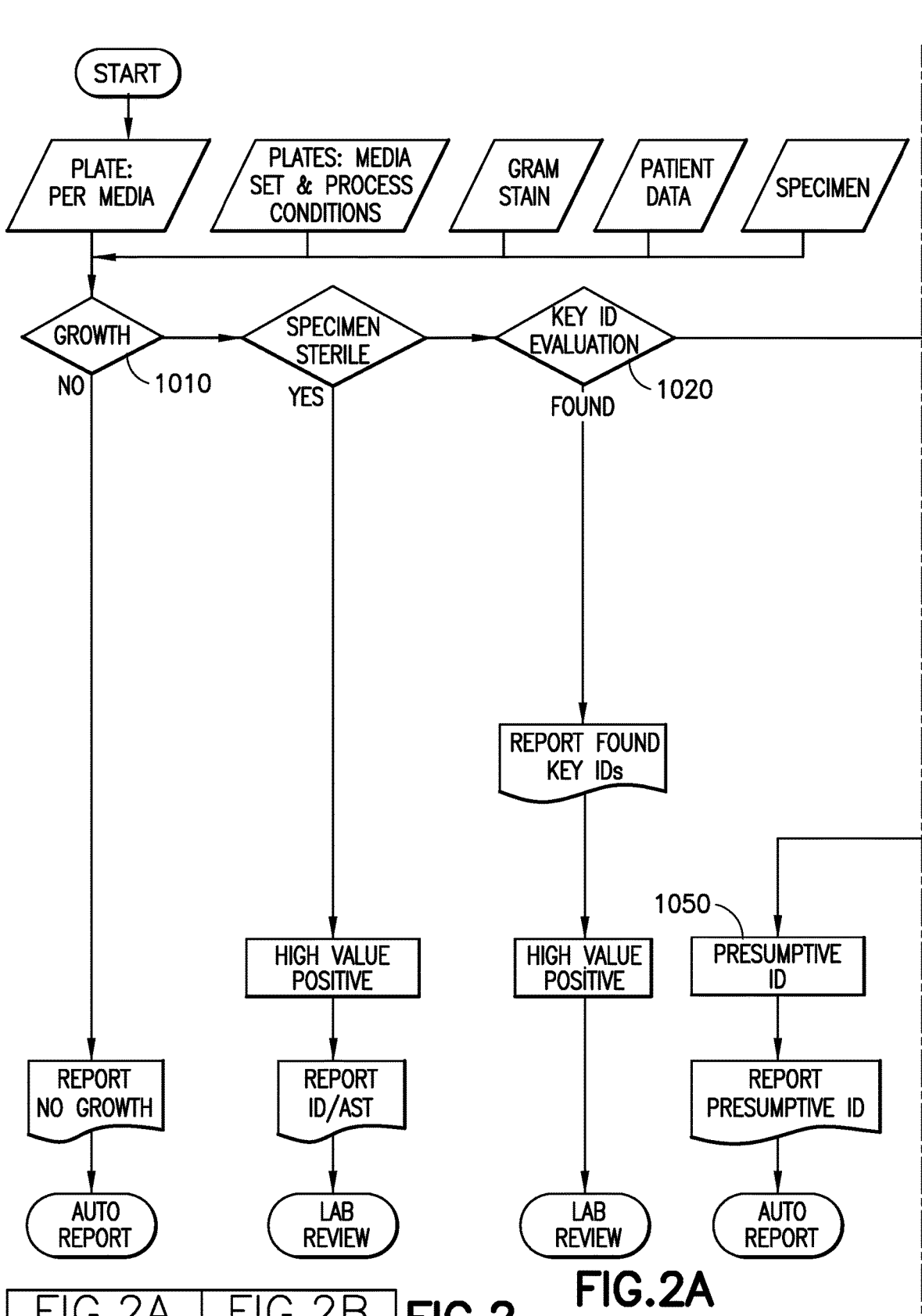
FIG. 2A is the portion of FIG. 2 that illustrates the growth and key ID Evaluation Modules.
Figure 2B:
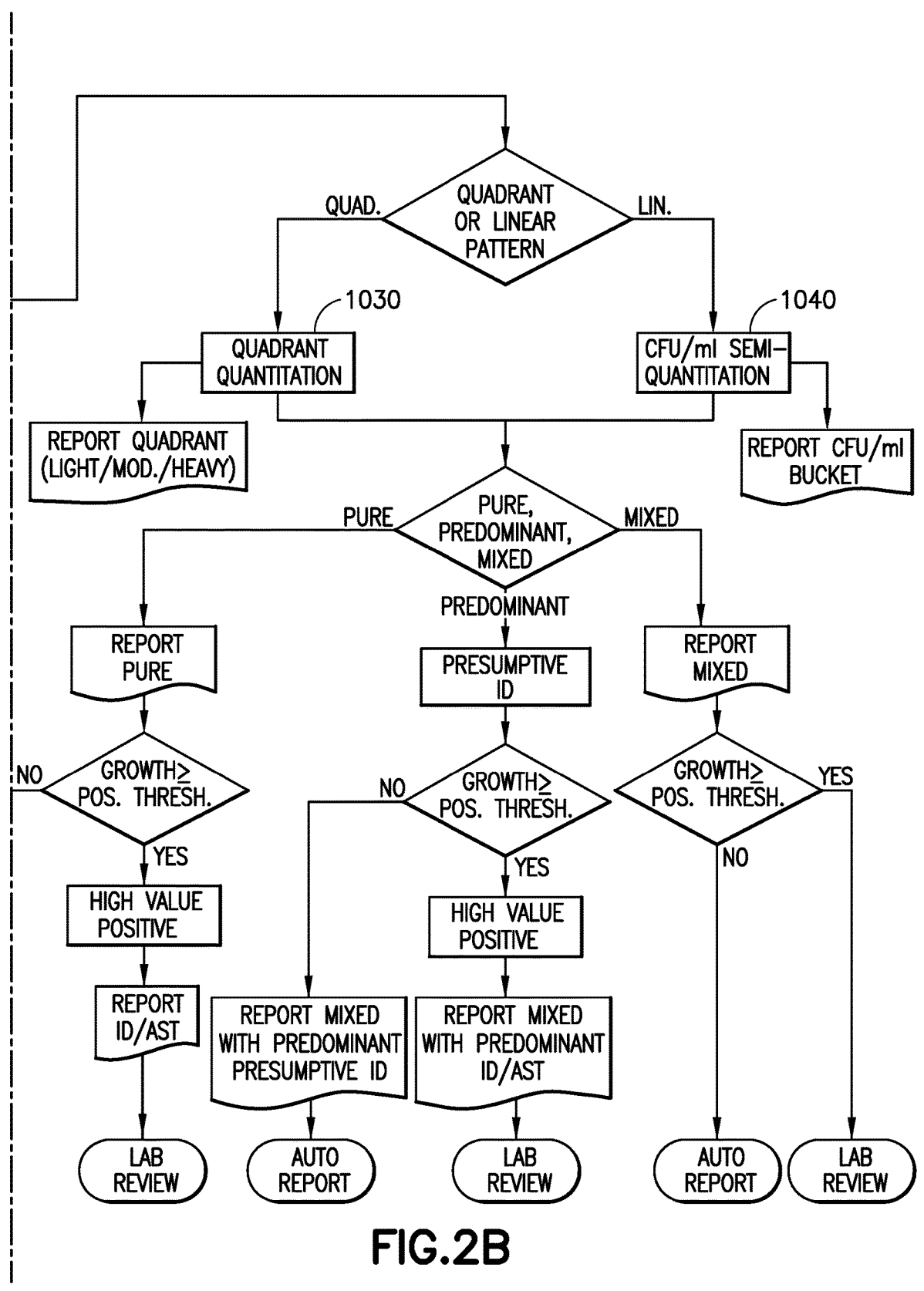
FIG. 2B is the portion of FIG. 2 that illustrates the quadrant quantitation and semi-quantitation modules.

Some examples of the algorithms and Modules (collections of synergistic algorithms) are generic (generally working across specimens, pathogens, media) and are summarized below and may be considered in relation to the processes of the illustration of FIG. 2 (FIG. 2A and FIG. 2B). As previously mentioned, the classification of functionality of the various applications helps to provide development of detection applications for various species and media.

1. Growth App/Module 1010A

Growth App 1010 (See FIG. 2A) may be directed to answering a simple question: is there anything growing that can be detected on this plate at this particular incubation time? The answer to this question will be a growth probability ranging from 0 to 1. Growth can be a module targeting any media, independent from dispense volume or streaking pattern. Growth may be detected as early as possible from pre-set imaging points. Rules specify whether to issue an alert based on specimen type and/or media. In some versions, gram stain results could also be integrated with App/Module where appropriate. In some cases, this may be implemented an Early Detection or Early Growth App/Module. Growth may be detected as early as possible (e.g., a detection window of 4 to 14 hours or more) from pre-set imaging points. Rules specify whether to issue an alert based on specimen type and/or media. In some versions, gram stain results could also be integrated here where appropriate.

2. Key ID App/Module 1020

A Key Id Module 1020 (See, FIG. 2A) may be aimed at identifying a species potentially growing on a given media. For each and every requested Key ID organism, the module may provide a list (with probabilities) of colony locations per Key ID ordered by decreasing probability. These colonies can then be picked manually or by an automated picking system.

In some versions, the system may include a Screening and Critical Pathogens module(s) developed on a pathogen basis. These modules may provide detection of specific pathogens, groups of pathogens or those with specific properties. The Screening Apps may be implemented to enable identification of specific pathogens on CHROMagar, and can be used for patient management as well as pathogen characterization e.g., MRSA, ESBL, CPE, VRE etc. CHROMagar may enable a collection of pathogens to be presumptively identified i.e., CHROMagar orientation for both Gram Negative (GN) and Gram Positive (GP) bacteria. Pathogen specific media may be used for specimens—such as SS media for *Salmonella, Shigella* from stool. Certain organisms may be presumptively identified or flagged on more generic media based on, for example, Hemolytic properties on blood agar, or unique morphologic properties on specific media. A potential collection of modules with pathogen x media capabilities is summarized in the Table of FIG. 4.

3. Quadrant Quantitation App/Module 1030

Based on a streaking pattern, e.g., a BD Kiestra™ Ino-qulA™ quadrant streaking pattern, this Quadrant Quantitation module 1030 (See, FIG. 2B), in case of detected growth, will provide a growth level being light, moderate or heavy. BD Kiestra™ InoqulA™ automates the processing of both liquid and non-liquid bacteriology specimens to help streamline workflow, enable standardized processes and ensure consistent and high-quality streaking for inoculation of solid growth media. The growth level will be returned as a vector of three probabilities (light, moderate or heavy) ranging on [0,1] and summing up to 1. For example, the Module may evaluate all plates to assess whether there is no growth or different amounts of growth (e.g., +, ++, +++) and whether any growth is pure, predominate or complex. A no Growth determination can result optionally in auto release, or batch release. In some cases, growth quantification (e.g., +, ++, +++) may be determined by three or more colonies in any particular quadrant.

With respect to growth type, the images/plates may be characterized as pure, predominant and complex. This may be based on a minimal number of isolated colonies of each type. For example, predominant growth may be greater than (or equal two) two colony types, where one type is greater than a factor (e.g., 10 times) the other(s). Complex may be greater than two colony types with no predominate isolate or if the isolate is not identifiable within a presumptive ID table such as the example of FIG. 3. Complex plates may be automatically flagged/passed to manual interpretation. Pure and predominant plate types could be automatically passed for further automated processing such as for having representatives of each colony type indicated, with rules that drive further workup (e.g., picking, ID and/or AST).

For example, a colony forming unit (CFU)/mL Quantitation App/Module 1040 (See, FIG. 2B) may be implemented. Based on InoqulA™ streaking pattern #4 (MonoPlates) or #6 (BiPlates), this module may provide a growth level being in <1, 1 to 9, 10 to 99, 100 to 999, ≥1000 CFU/media on plate. The growth level may be returned as a vector of 5 probabilities ranging on [0,1] and summing up to 1. To get equivalent CFU/ml buckets units, the dispense volume may need to be considered.

In general, the Quantification module may, in some versions, determine if growth is due to a single growing organism, a predominant organism or a mixture of (multiple) organisms. A pure organism may be deemed to be an organism responsible for ≥99% of the observable/imageable growth. A predominant organism may be an organism responsible for (90%, 99%) of the observable/imageable growth. A purity level may be returned as a vector of probabilities (e.g., 3 probabilities as pure, predominant, complex) ranging on [0,1] and summing up to 1. In the case of pure or predominant growth up to five colony locations for the main organism will be given in decreasing probabilities.

Examples of responses to determined quantification are as follows:

1) An image of a specimen on a plated media is determined to have greater than a predetermined threshold (100,000 CFU/mL) of mixed flora. The response of the App to this determination is to flag this plate as a complex plate, because the plate has over the threshold amount of mixed flora and recommend manual review of the plate. Such a determination is not made in the context of media or taxa so this is an App of broad applicability and not limited in deployment to specific media or taxa on the plate.

2) An image is evaluated and determined to exhibit no growth for 24 hrs. If the specimen is classified as a critical specimen the App issues a preliminary report of no growth and either recommends or controls the re-incubation of the plate for another 24 hours. If a subsequent image detects no growth in 48 hours, the App sends a final report to the user of no growth after 48 hours. The App either recommends or controls discarding the plate 3) An image of a specimen on a plated media is determined to have greater than a predetermined threshold (100,000 CFU/mL) of a pure growth and a colony size that exceeds 0.5 mm. The response of the App is to issue an instruction or control the pick of colony for ID and AST testing. The App will flag the specimen for review by the technician and will send the greater than 100,000 CFU/mL report to the physician associated with the specimen.

4) An image of a specimen is determined to reveal the presence of MRSA by the App. The App sends a report that MRSA is detected and adds the specimen to a positive MRSA work list. If the App determines that the size of the MRSA colony exceeds a threshold (e.g. greater than 0.5 mm) the App will issue an instruction or control sending the sample for ID and AST testing. As noted elsewhere herein, ID and AST have their own specimen work up and evaluation. As such, ID and AST systems and apparatus are typically downstream of the incubation/imaging apparatus (e.g. Kiestra™ ReadA compact).

5) An image of a specimen classified as ESBL is determined to show no growth. The App will issue a final report that no ESBL isolate was detected and will issue an instruction to discard or control discard of the plate.

6) An image of specimen classified as sputum is identified as having mixed flora (therefore a complex plate) that exceeds the threshold amount. When the App determines that the plate is complex it issues an instruction for a technician to review the plate. Note that different thresholds for mixed flora that trigger the requirement for manual review might be deployed depending on specimen classification.

7) An image of a specimen classified as critical on blood agar is determined to reveal growth. In such an instance, the critical specimen App would fire and send an alert to the physician associated with the specimen and cause the specimen to be added to the critical sample work list. If the App determines that a colony greater than a threshold size (i.e. greater than 0.5 mm) and specimen is classified as being disposed on MacConkey agar, then the App causes the specimen to be sent to auto pick for MALDI and for Gram negative AST. The App will also send a report indicating that a Gram-negative specimen has been isolated.

8) An image of a specimen reveals a colony number that is greater than 100,000 CFU/mL and classifies the image as pure and having a colony size greater than a predetermined threshold (e.g. greater than 0.5 mm). In response, the App causes the specimen to be auto picked for AST, causes the specimen to be added to the positive review list by a technician and causes a report to be sent to the physician associated with the sample that indicates that more than 100,000 CFU/mL of a colony was detected from the sample. Further, if the AST results reveal that the picked colony is resistant to Carbapenem, then the App causes a molecular confirmatory test to be performed.

9) An image of a specimen is determined to possess heavy predominant growth. In response, the App causes the growth to be auto picked and a suspension prepared for performing MALDI on the picked sample. If the MALDI identifies the colony as *E. coli*, then the App causes the sample to be further evaluated for Gram Negative AST (using either the MALDI suspension or a new pick of the colony).

In some versions, growth detection may be implemented as two modules where one evaluates plates to determine growth/no growth and another module evaluates growth quantity (+, ++, +++) in 3 or more colonies in any particular quadrant. For example, a first module evaluates an image of a critical, normally sterile specimen. If that evaluation reveals growth at a predetermined time point, and determines that a colony size is greater that a predetermined threshold size, then the App identifies coordinates of representative colonies and issues instructions to the imaging apparatus (e.g. ReadA) that the plate is to be moved to an apparatus that will auto pick the identified colony. The picked colony is resuspended in a solution to a predetermined density for further testing in, e.g., a molecular diagnostic apparatus or test (e.g., PCR, Sequencing).

4. Presumptive ID App/Module 1050

In case of pure or predominate growth, a Presumptive ID module 1050 (See, FIG. 2A) may identify the main organisms potentially growing on a given media using a set of identification algorithms based on the training with the Data Lake. This module may provide/output a name of a highest ranking (e.g., probability) organism (or organism groups) and up to five colony locations ranked from highest to lowest probability for that identification. These algorithms enable identification of specific species on specific media types where any number of colonies are present and considered clinically significant.

For example, the media and colony identities may be those indicated in the Table of FIG. 3. Rules that action workup of these colonies can be included in the Module. As an example of a specific IDApp, a urine culture App (UCA) and Chrom ID App could enable presumptive ID on Orientation CHROMagar from urines for those organisms claimed by the media. Rules would apply the ability to auto report/ auto release (or batch), and downstream workup (e.g., automatic picking, testing, etc.). In some cases, rules may determine High Value Positives to flag plates that should be rapidly reviewed and directed for further process by a work list or automated pick, etc.

4.1 Purity Plate App/Module

In some versions, the system may implement a purity plate module. Pure, predominant and complex plates may require a minimal number of isolated colonies in each. Predominant growth has typically greater than two colony types, where one colony type is greater than ten times the other colony type. Complex type typically has greater than two colony types with no predominate isolate or if the isolate is not identifiable (presumptive ID table below). Complex plates are typically manually interpreted. Thus, the module may classify the plate image according to whether it is pure, predominant (which can be slightly mixed) and/or complex.

4.2 AutoSelect ID/AST Module

Pure and predominant plates can have representatives of each colony type indicated by the Purity Plate Mod with associated Rules that drive further workup as set forth in the examples above. A pre-determined number of each colony type could be designated for automatic identification (ID) and AST workup on an ID/AST module that may involve an automatic picking system/robot.

5. Kirby-Bauer (KB) Zone Diameter Measurement App Module

Some embodiments may utilize an optional measurement App. Such an App may leverage existing imaging capabilities and the AST Expert Systems to provide zone measurements. Optionally these measurements may be linked to expert systems to provide interpretations. Opportunities also exist for a version of this App for Early zone measurements for particular drug/organism combinations and for zones on media plated directly from positive blood culture. Such algorithms may be based on metadata and/or images of the Data Lake.

In some versions, this App would leverage existing imaging capabilities and an AST Expert System to provide zone measurements and Abx Disk identification. Optionally these measurements could be linked to expert systems to provide guidance on an antibiotic susceptibility profile for a pathogen isolated from the patient and guidance on treatment/ response. In some versions, implementations of this App may provide early zone measurements for particular drug/ organism combinations and for zones on media plated directly from positive blood culture. Some Apps may include expert systems (interpretations) and could be facilitated significantly with the Data Lake being stocked, monitored, audited appropriately and with required metadata and images.

Although a system 100 may include any one or more of the above imaging related modules/Apps, in some versions a particular segmentation of functionality of the modules may be implemented by the following set of discrete modules/Apps: (a) Quadrant-Quantitation; (b) Detection of No Growth; (c) Purity Plate: # Colony Types (e.g., pure, Predominant, Complex) (d) Screening (e.g., CHROMagar i.e. MRSA); (e) Critical pathogens; (f) Early Growth Detection; (g) Auto Select ID/AST and (h) Zone measurement Kirby-Bauer.

Imaging Apps and Launch Packages

The system 100, providing the combination of algorithms/ modules/rules, the Data Lake, and the ability to extract predetermined subsets of data, can enable an on-demand ability to rapidly mature algorithms and develop Apps. As an example, Apps may be developed based on specimen type and may be implemented with a collection of Apps. The strategy to implement a collection of Apps is influenced by many factors: supporting software launch cadence; value of individual Apps vs Apps being together; the availability of certain algorithms or specimen/plate/organism types in the Data Lake, etc.

An example may be considered in relation to the following table:

TABLE 1

| | Exemplary Modules and Their Functions | |
|---|---|---|
| Module Number | Module Name | Function |
| 1 | Urine Culture Quantitation | Quantitation into 5 buckets; apply user threshold rules |
| 2 | Urine Culture Auto- Negative Release | Auto Release (in Europe) of No Significant Growth Plates |
| 3 | Urine Culture Quantitation-BiPlate | Quantitation into 5 buckets on each half with rules |
| 4 | Urine Culture Early Growth Detection | Earliest Growth Detected on Plate Provides a Notification to a User |

TABLE 1-continued

Exemplary Modules and Their Functions

| Module Number | Module Name | Function |
|---|---|---|
| 2.1 | Urine Culture Batch-Negative Release | Batch Release (in the US) of No Growth Plates |
| 5 | Urine Presumptive ID | Orientation CHROMagar-based ID of claimed taxa |

In this specimen-based example, a series of 5 different Modules concerns one specimen type. Apps validated against a particular specimen type is one way to package functionality, however, an Exponential approach will also allow other options. For example, Surveillance Apps will allow launch by particular targeted organism (MRSA, *Streptococcus, Shigella*); Quantitation Apps could be packaged by media type (quantity of the sample on blood agar, independent of specimen), etc. In this sense, however, certain Apps will likely have minimal value for certain Specimens (i.e., quantity of the sample on nonselective media with sputum, given high normal flora levels). Note that the Apps can be delimited by region with specific rules and specific functions limited to the geographic region from which the specimen under evaluation was obtained. Table 1 identifies functions specific to clinical requirements particular to the United States (US) and Europe (EU).

Thus, potential Apps may be segregated into two-high-level buckets. A first bucket collection may be considered screening and key identification Apps. Such Apps typically target specific organisms on CHROMagars, or for high-value pathogens on, for example, Blood agar. Each of these are discrete and can be prioritized for development with minimal impact to other Apps or specimen types and launched individually if desired. Similarly, the Kirby-Bauer zone App is generally independent of the next generation Apps ("Next Gen App"), which have associated algorithms that can be independently prioritized. Additionally, as new CHROMagars (i.e., vancomycin resistant enterococci (VRE)) become available, appropriate specimens can be run to populate the Data Lake and be added to this list. If targeted isolates are relative rare, the Data Lake may be supplemented with contrived (spiked specimen) samples. Additional example screening and Key ID Apps are illustrated in the following Table.

TABLE 2

App Classification, Construction, Function and Output

| App Category | App Classification | App Function | Type of Specimen | Output/Instruction From App | Data Required to Train and Run App |
|---|---|---|---|---|---|
| Critical Pathogen | Group B Strep on CHROMagar Orientation | Auto Negative Report for Group B Strep initial batch review and release auto negative release in the US with clinical submission | urine | Auto-Neg (EU only) Batch - US and EU Auto Neg - US FDA | Training Data; data lake validation; clinical submission |
| Critical Pathogen | MRSA on CHROMagar MRSA II | Flag growth for MRSA initial batch review and release; auto negative release in the US with clinical submission | Nasopharyngeal perirectal | Auto-Neg (EU only) Batch - US and EU Auto Neg - US FDA | Training Data; data lake validation; clinical submission |
| Critical Pathogen | Group B Strep on TSA Blood Agar | Flag growth for Group B Strep initial batch review and release auto negative release in US with clinical submission | Vaginal | Auto-Neg (EU only) Batch - US and EU Auto Neg - US FDA | Training Data; data lake validation; clinical submission |
| Critical Pathogen | Group A Strep on Selective Strep Agar and Blood Agar | Flag growth for Group A Strep initial batch review and release auto negative release in US with clinical submission | Nasopharyngeal perirectal | Auto-Neg (EU only) Batch - US and EU Auto Neg - US FDA | Training Data; data lake validation; clinical submission |
| Critical Pathogen | CHROMagar Carbapenems | Flag growth for CPE initial batch review and release auto negative release in US with clinical submission | Nasopharyngeal perirectal | Auto-Neg (EU only) Batch - US and EU Auto Neg - US FDA | Training Data; data lake validation; clinical submission |

TABLE 2-continued

App Classification, Construction, Function and Output

| App Category | App Classification | App Function | Type of Specimen | Output/Instruction From App | Data Required to Train and Run App |
|---|---|---|---|---|---|
| Critical Pathogen | CHROMagar ESBL | Flag growth for ESBL initial batch review and release auto negative release in US with clinical submission | Nasopharyngeal perirectal | Auto-Neg (EU only) Batch - US and EU Auto Neg - US FDA | Training Data; data lake validation; clinical submission |
| Critical Pathogen | *Salmonella* and Shigella on Hecktoen, XLD and SS agar | Flag growth for *Salmonella* and Shigella initial batch review and release auto negative release in US with clinical submission | Stool | Auto-Neg (EU only) Batch - US and EU Auto Neg - US FDA | Training Data; data lake validation; clinical submission |
| Critical Pathogen | N. gonorrhea on Thayer Martin media | Flag growth for N gonorrhea initial batch review and release auto negative release in US with clinical submission | urogenital | Auto-Neg (EU only) Batch - US and EU Auto Neg - US FDA | Training Data; data lake validation; clinical submission |
| Critical Pathogen | Haemophilus on Chocolate Agar | Flag growth for Haemophilus initial batch review and release auto negative release in US with clinical submission | Respiratory | Auto-Neg (EU only) Batch - US and EU Auto Neg - US FDA | Training Data; data lake validation; clinical submission |
| KB zone | Zone measurement linked to Abx code | Zone measurement, user review and release | Colony to KB | EU US | Training Data; data lake validation. |
| KB zone SIR | Zone measurement linked to Abx code and simple look up table for SIR | Zone measurement, user review and release | Colony to KB | EU US | Training Data; data lake validation. |
| KB zone expert | Zone + Abx code linked to an Expert System defined organism x drug | Zone measurement linked to EuCAST Expert System may require new rules for certain organism x drug, Abx ID; Zone measurement linked to FDA/CLSI Expert System | Colony to KB | EU US | Training Data; data lake validation, organism x drug (EU); For US add clinical software submission |
| KB early zone | Zone + Abx code at 10-12 hours | Zone measurement, user review and release | Colony to KB | EU US | Training data, digital lake validation, organism x drug (EU); for US add manual v. digital submission. |
| KB early zone expert | Zone measurement; Expert System defined organism x drug | Zone measurement linked to EuCAST Expert System may require new rules for certain organism x drug, Abx ID; Zone measurement linked to FDA/CLSI Expert System | Colony to KB | EU US | Training data, digital lake validation, organism x drug (EU); for US add clinical submission software. |
| KB zone-positive blood culture | Zone measurement; Expert System defined organism x drug | Zone measurement linked to novel expert system | Colony to KB | EU US | Training data, database validation, expert rules (EU) for US add FDA submission and organism x drug |

It can be observed from Table 2 that Apps can be quite specific and that the outputs can depend on specimen classification (i.e. type of specimen, US region or EU region, etc.). Table 2 also illustrates at a high level, the type of data used to train the App.

A second bucket collection of Apps use more generic algorithms and can be prioritized and grouped for launch by several criteria. A summary of examples of these Apps is provided in Table 3 below. In essence, each cell in Table 3 represents an App. Cells in the Table below that share the same number are appropriate capabilities for that specimen type where the shared cell numbers are reasonably packaged together in a common module. With this model, there are 8 additional launch packages/modules.

TABLE 3

| Capability | Urine | Sterile Fluids and Tissue | Superficial Wounds | Respiratory | Throat | Gastro-Intestinal | Urogenital |
|---|---|---|---|---|---|---|---|
| No Growth | 1 | 1 | 1 | 2 | 2 | 2 | 2 |
| Quadrant Growth Score (+, ++, +++) | 2 | 3 | 6 | 7 | 7 | 8 | 9 |
| Plate purity (pure, predominant, complex | 5 | 3 | 6 | 7 | 7 | 8 | 9 |
| Presumptive ID on pure, predominant plates | 5 | 3 | 6 | 7 | 7 | 8 | 9 |
| Early Growth Detection | 5 | 4 | 4 | 2 | 2 | 2 | 2 |
| Auto picking pure, predominant | 5 | 3 | 6 | 7 | 7 | 8 | 9 |

Example imaging modules may be considered with reference to the following table:

TABLE 4

List of Exemplary Modules

Imaging Module

| Mod 1. | UCA 1.0 Urine Culture Semi-Quantitation |
|---|---|
| Mod 2. | UCA 1.0 Urine Culture Auto-Negative Release Eu |
| Mod 3. | UCA 1.5 Urine Culture Semi-Quantitation-BiPlates |
| Mod 4. | UCA 1.5 Urine Culture Early Growth Detect |
| Mod 2.1 | UCA 1.5 Urine Culture batch-Negative Release (US) |
| Mod 5. | UCA 1.8 Presumptive ID BBL Orientation CHROMagar for 6 groups; Group B Strep flag |
| Mod 6. | UCA 1.8 Pure/Predominant/Complex on BBL Orientation CHROMagar |
| Mod 6.2 | UCA 2.0: UCA 1.8-autorelease US. 510K approval. 25 mp camera launch |
| Mod 7. | Surveillance: MRSA on BBL CHROMagar. Batch Release EU/US |
| Mod 8. | Surveillance: Carbepenem producing Enterobacteriaciae (CPE) on BBL CHROMagar |
| Mod 9. | Surveillance: ESBL on BBL CHROMagar |
| Mod 9. | Critical Specimens: Early Growth (sterile fluids, superficial wound, tissue, urine) |
| Mod 10. | Critical Specimens: Presumptive ID |
| Mod 11. | Critical Specimens: Quadrant quantitation, |
| Mod 12 | Critical Specimens: Pure/Predominant/Complex |
| Mod 13. | Critical Specimens: No Growth Detection (user defined time pts). Batch/Auto |
| Mod 14. | Critical Specimens: Auto Select ID/AST (Wagtail) |
| Mod 15. | KB Zone (disk ID, Zone size) manual interpretation |
| Mod 16 | KB Zone SIR (susceptible, intermediate, resistant) manual release |
| Mod # | Critical Pathogen: Group A Strep on Selective Strep Agar, and Blood Agar |
| Mod # | Respiratory: Quadrant quantitation; |
| Mod # | Respiratory: Pure/predominant/complex |
| Mod # | Respiratory: Presumptive ID |

TABLE 4-continued

List of Exemplary Modules

Imaging Module

| Mod # | Respiratory: Auto Select ID/AST |
|---|---|
| Mod # | Respiratory: Critical Pathogen: Haemophilus on chocolate agar |
| Mod # | Stool: Negative growth batch report from enrichment culture on selective agar |
| Mod # | Stool: Negative growth batch reporting from primary culture |
| Mod # | Stool: Quadrant quantitation |
| Mod # | Stool: Pure/Predominant/Complex |

TABLE 4-continued

List of Exemplary Modules

Imaging Module

| Mod # | Stool: Critical Pathogen: *Salmonella* and Shigella on Hecktoen, XLD, and SS media |
|---|---|
| Mod # | Stool: Auto Pick (Wagtail) |
| Mod # | KB-Zone-expert System. CLSI (Clinical and Laboratory Standards Institute)/EUCAST guidelines. SIR |

EUCAST is the European Committee on Antimicrobial Susceptibility Testing. In one example of a process integrated with one or more Apps for specimen evaluation and process control, a specimen is inoculated onto a plated media using BD Kiestra™ InoqulA. The specimen is streaked onto the media using a predetermined pattern which is tracked as part of metadata via the bar code. The streaked sample is conveyed into BD Kiestra™ ReadA compact where it is incubated and imaged at times determined by the App. The images obtained by ReadA at the appointed time is analyzed by the App to determine if the specimen on the plate is pure. Further work up of the specification is performed based on the results of the determination. The image is evaluated to identify the coordinates of the selected colonies. The App can convey those coordinates to an apparatus (or technologist). The App can issue instructions to convey the specimen to the apparatus in which the colony will be picked. The App can further coordinate or control the picking of the colonies and conveying the picked colonies to another platform where ID of the pathogen is performed. In one example ID is performed by MALDI. As described elsewhere herein, a sample is evaluated by MALDI by placing the picked sample into suspension and inoculating a MALDI plate with the suspension. The App can also coordinate or control transfer of the colony suspension to BD Kiestra™ InoqulA. There the suspension can be inoculated onto another type of culture media (e.g., Mueller Hinton) using a "spread pattern" and then moved to an AST testing apparatus where predetermined antibiotic disks (e.g. BD BBL™ Sensi-DiscsT™) are place on the culture. The plate carrying the inoculated specimen and the antibiotic disks is then conveyed to a ReadA compact under coordination and control of the App. The ReadA obtains images and provides those images to the App, the results of which are conveyed from the App to an Expert System for analysis of the resulting antibiotic disk zones and interpretation of the results. The Expert System then conveys the results of the analysis to the clinical lab staff Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for processing a biological sample comprising:
   obtaining a biological sample;
   combining the biological sample with nutrient media;
   incubating the biological sample;
   obtaining a digital image of the incubated biological sample;
   classifying the digital image according to analytical criteria selected from the group consisting of specimen origin information, clinical sample criteria, process materials and process conditions;
   obtaining data from historical digital images of incubated biological samples on nutrient media that share at least one of the analytical criteria assigned to the digital image; and
   using the historical digital image data to output an instruction to a user for further processing of the biological sample, wherein the further processing is selected from the group consisting of identification testing, antibiotic susceptibility testing or both.

2. The method of claim 1, wherein the analytical criteria comprises specimen origin information, and wherein the specimen origin information comprises geographic information regarding the biological sample source and the type of biological sample.

3. The method of claim 1, wherein the analytical criteria comprises process materials, and wherein the process materials comprise type of nutrient media.

4. The method of claim 1, wherein the historical digital image data is classified by at least one of specimen type, organism taxa or culture media type.

5. The method of claim 1, further comprising, after obtaining the digital image of the incubated biological sample, analyzing the digital image data and determining, from the analyzed data if the digital image reflects microbial growth.

6. The method of claim 5, wherein, in response to a determining that the digital image does not show microbial growth, outputting an indication of no microbial growth.

7. The method of claim 5, wherein, in response to determining that there is an indication of microbial growth, determining if the specimen is a sterile specimen and identifying one or more coordinates of a colony of microorganisms in the digital image that was a basis for the indication of microbial growth.

8. The method of claim 7, wherein, in response to determining that the specimen is sterile, indicating that the specimen is a high value positive and sending instructions to further process the specimen.

9. The method of claim 8, further comprising communicating the coordinates of a colony to a module that communicates the coordinates to a picking apparatus that will pick the colony from the biological sample.

10. The method of claim 9, further comprising transferring the biological sample to the picking apparatus and picking the colony from the biological sample wherein the steps of transferring and picking are controlled by the module.

11. The method of claim 7, wherein, in response to determining that the specimen is not sterile, comparing the historical digital image data with the digital image data to identify a specific predetermined species of microorganism in the digital image of the incubated biological sample.

12. The method of claim 11, wherein the comparing is performed by a module, and, if the module determines that the specific predetermined species of microorganism is present in the image data, the module reports the identification of the specific predetermined species.

13. The method of claim 12, further comprising flagging the specimen for further review.

14. The method of claim 7, further comprising comparing the historical digital image data with the digital image of the incubated biological sample and determining an amount of microbial growth wherein the comparing and determining steps are performed in a module in communication with an imaging apparatus that obtained the digital image of the incubated biological sample.

15. The method of claim 7, further comprising determining if the microbial growth on a plate is one of pure colonies, predominant colonies, or complex colonies by communicating the digital image of the incubated biological sample to a module that determines a growth level as a vector of three probabilities.

16. The method of claim 15, wherein, in response to a determination that the colony is pure, the method further comprises:
   reporting, from the module, that the plate is pure; and
   determining, by the module, if the growth exceeds a predetermined threshold growth.

17. The method of claim 16, wherein, if the module determines that the growth exceeds the predetermined threshold growth, the method further comprises:
   identifying the sample as a high value positive;
   alerting a user of the high value positive;
   identifying the coordinates of the high value positive;
   communicating the coordinates of a colony to a module that communicates the coordinates to a picking apparatus that will pick the colony from the biological sample; and
   transferring the biological sample to the picking apparatus and picking the colony from the biological sample wherein the steps of transferring and picking are controlled by the module.

18. The method of claim 17, wherein, if the module determines that the growth does not exceed the predetermined threshold the module provides a presumptive identification of the colony based on comparing an image of the colony from them digital image of the incubated biological sample provided to the module with the historical digital image data accessed by them module, the module performing the further step of:

reporting the presumptive ID to a user.

19. The method of claim 15, wherein, in response to a determination that the colony is predominant, the module provides a presumptive identification of the colony based on comparing an image of the colony from them digital image of the incubated biological sample provided to the module with the historical digital image data accessed by them module, the module performing the further step of:

reporting the presumptive ID to a user.

20. The method of claim 19, the method further comprising:

determining, by the module, if the growth exceeds a predetermined threshold growth.

21. The method of claim 20, wherein, if the module determines that the growth exceeds the predetermined threshold growth, the method further comprises:

identifying the sample as a high value positive;

alerting a user of the high value positive;

identifying the coordinates of the high value positive;

communicating the coordinates of a colony to a module that communicates the coordinates to a picking apparatus that will pick the colony from the biological sample;

transferring the biological sample to the picking apparatus and picking the colony from the biological sample wherein the steps of transferring and picking are controlled by the module; and alerting a user that further review is required.

22. The method of claim 20, wherein, if the module determines that the growth does not exceed the predetermined threshold the module performs the further step of:

reporting the presumptive ID to a user.

23. The method of claim 15, wherein, in response to a determination that the colony is complex, the method further comprises:

reporting, from the module, that the plate is complex; and determining, by the module, if the growth exceeds a predetermined threshold growth.

24. The method of claim 23, wherein, if the module determines that the growth exceeds the predetermined threshold growth, the method further comprises:

alerting a user that further review is required.

25. The method of claim 17, wherein, if the module determines that the growth does not exceed the predetermined threshold the module performs the further step of:

reporting to a user that the complex sample does not meet or exceed the predetermined threshold growth.

* * * * *